United States Patent [19]

Nishida et al.

[11] Patent Number: 4,562,213

[45] Date of Patent: Dec. 31, 1985

[54] CERTAIN PHENOXY-BENZYLOXY ETHER DERIVATIVES AND AN INSECTICIDAL AND/OR ACARICIDAL COMPOSITION CONTAINING THE SAME AND METHODS OF USE

[75] Inventors: Sumio Nishida, Takarazuka; Noritada Matsuo, Itami; Kazunori Tsushima, Nishinomiya; Makoto Hatakoshi, Minoo; Masachika Hirano, Osaka, all of Japan

[73] Assignee: Sumitomo Chemical Company, Limited, Osaka, Japan

[21] Appl. No.: 491,727

[22] Filed: May 5, 1983

[30] Foreign Application Priority Data

May 12, 1982 [JP] Japan .................................. 57-80510
Dec. 13, 1982 [JP] Japan .................................. 57-218819

[51] Int. Cl.$^4$ .................... C07D 213/64; C07C 43/20; A01N 43/40; A01N 31/14
[52] U.S. Cl. .................................. 514/721; 514/345; 514/464; 546/301; 546/302; 546/270; 568/636; 568/637
[58] Field of Search ................ 568/636, 637; 546/301, 546/302, 270; 424/263, 341; 514/345, 464, 721

[56] References Cited

FOREIGN PATENT DOCUMENTS

| | | | |
|---|---|---|---|
| 0104908 | 4/1984 | European Pat. Off. ............ | 514/464 |
| 2342953 | 3/1977 | France ................................. | 568/631 |
| 2481695 | 11/1981 | France ................................. | 549/497 |
| 56-154427 | 11/1981 | Japan ................................... | 568/636 |
| 57-072928 | 7/1982 | Japan ................................... | 549/497 |
| 2085006 | 4/1982 | United Kingdom ................ | 568/636 |

*Primary Examiner*—Alan L. Rotman
*Attorney, Agent, or Firm*—Stevens, Davis, Miller & Mosher

[57] ABSTRACT

Ether compounds of the general formula,

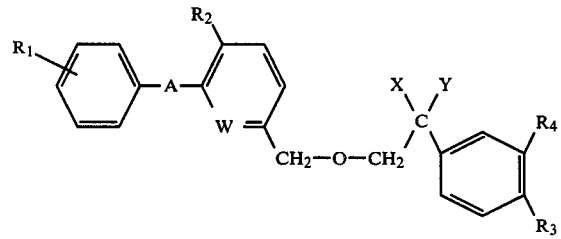

wherein W represents CH group or nitrogen atom, and (1) when W is the CH group, $R_1$ represents hydrogen atom, fluorine atom, chlorine atom, bromine atom or methyl group, $R_2$ represents hydrogen atom or fluorine atom, $R_3$ and $R_4$ are same or different and represent hydrogen atom, a halogen atom, a $C_{1-4}$ alkyl, a $C_{1-4}$ alkoxyl, difluoromethoxy or 2,2,2-trifluoroethoxy group, or represent, taken together, methylenedioxy group, A represents oxygen atom, methylene group or imino group, and when the A represents oxygen atom or methylene group, X and Y represent, taken together, ethylene group or 1,1-difluoroethylene group and when the A represents imino group, both X and Y represent methyl group or represent, taken together, ethylene group or 1,1-difluoroethylene group, and (2) when W is the nitrogen atom, both $R_1$ and $R_2$ represent hydrogen atom, $R_3$ and $R_4$ are as define above, A represents oxygen atom, and both X and Y represent methyl group or represent, taken together, ethylene group or 1,1-difluoroethylene group.

The ether compounds of the present invention are useful as an active ingredient of an insecticidal and/or acaricidal composition.

19 Claims, No Drawings

CERTAIN PHENOXY-BENZYLOXY ETHER DERIVATIVES AND AN INSECTICIDAL AND/OR ACARICIDAL COMPOSITION CONTAINING THE SAME AND METHODS OF USE

The present invention relates to ether compounds represented by the formula (I),

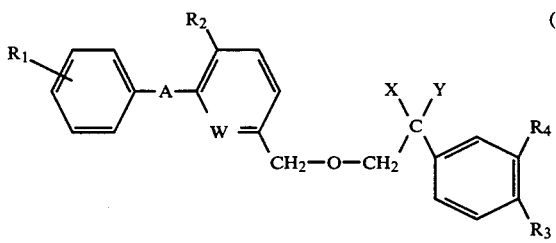

wherein W represents CH group or nitrogen atom, and
(1) when W is the CH group, $R_1$ represents hydrogen atom, fluorine atom, chlorine atom, bromine atom or methyl group, $R_2$ represents hydrogen atom or fluorine atom, $R_3$ and $R_4$ are same or different and represent hydrogen atom, a halogen atom, a $C_{1-4}$ alkyl, a $C_{1-4}$ alkoxyl, difluoromethoxy or 2,2,2-trifluoroethoxy group, or represent, taken together, methylenedioxy group, A represents oxygen atom, methylene group or imino group, and when the A represents oxygen atom or methylene group, X and Y represent, taken together, ethylene group or 1,1-difluoroethylene group and when the A represents imino group, both X and Y represent methyl group or represent, taken together, ethylene group or 1,1-difluoroethylene group, and (2) when W is the nitrogen atom, both $R_1$ and $R_2$ represent hydrogen atom, $R_3$ and $R_4$ are as defined above, A represents oxygen atom, and both X and Y represent methyl group or represent, taken together, ethylene group or 1,1-difluoroethylene group, their production and an insecticidal and/or acaricidal composition containing them as an active ingredient.

As a result of an extensive study to develop excellent insecticidal and/or acaricidal composition, the present inventors found that the ether compound represented by the foregoing formula (I) has a high insecticidal and/or acaricidal effect, and thus attained to the present invention.

As specific examples of insect pests against which the compounds of the present invention are particularly effective, there are given for example Hemiptera such as planthoppers, leaf-hoppers, aphids, bugs, etc., Lepidoptera such as diamond-back moths, armyworms and cutworms, etc., Coleoptera such as maize weevil (*Sitophilus Zeamais*), Japanese beetle (*Popillia japonica*), etc., Diptera such as common mosquito (*Culex pipiens pallens*), housefly (*Musca domestica*), etc., Orthoptera such as shortwinged rice grasshopper (*Oxya japonica*), etc., and Diclyoptera such as German cockroach (*Blattella germanica*) and the like.

The compounds of the present invention are obtained by reacting a halide represented by the formula (II),

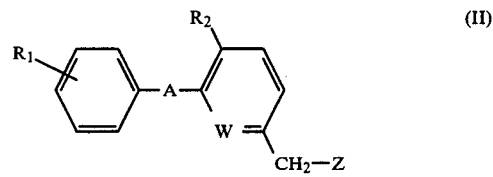

wherein $R_1$, $R_2$, A and W are as defined above and Z is a halogen atom, with an alkali metal salt of an alcohol represented by the formula (III),

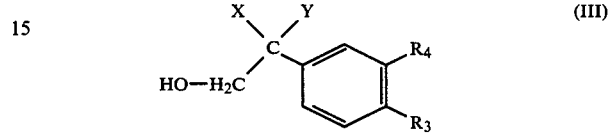

wherein X, Y, $R_3$ and $R_4$ are as defined above. More particularly, the compounds can for example be produced by reacting the alcohol represented by the foregoing formula (III) with an alkali metal hydride in an aprotic polar solvent (e.g. dimethylformamide, dimethyl sulfoxide) to obtain an alkali metal salt of the alcohol, and reacting the resulting salt with a halide represented by the formula (II) at 0° C. to 50° C. for 1 to 12 hours.

As the alcohol represented by the formula (III), the following compounds may be given:
2,2-Dimethyl-2-(4-fluorophenyl)ethanol
2,2-Dimethyl-2-(4-chlorophenyl)ethanol
2,2-Dimethyl-2-(4-bromophenyl)ethanol
2,2-Dimethyl-2-(3,4-dichlorophenyl)ethanol
2,2-Dimethyl-2-(4-methylphenyl)ethanol
2,2-Dimethyl-2-(4-ethylphenyl)ethanol
2,2-Dimethyl-2-(4-tert-butylphenyl)ethanol
2,2-Dimethyl-2-(4-methoxyphenyl)ethanol
2,2-Dimethyl-2-(4-ethoxyphenyl)ethanol
2,2-Dimethyl-2-(4-n-propyloxyphenyl)ethanol
2,2-Dimethyl-2-(4-iso-propyloxyphenyl)ethanol
2,2-Dimethyl-2-(4-n-butyloxyphenyl)ethanol
2,2-Dimethyl-2-(4-difluoromethoxyphenyl)ethanol
2,2-Dimethyl-2-[4-(2,2,2-trifluoroethoxy)phenyl]ethanol
2,2-Dimethyl-2-(3,4-methylenedioxyphenyl)ethanol
2,2-Dimethyl-2-(3-chlorophenyl)ethanol
1-(4-Fluorophenyl)cyclopropyl-1-carbinol
1-(4-Chlorophenyl)cyclopropyl-1-carbinol
1-(4-Bromophenyl)cyclopropyl-1-carbinol
1-(3,4-Dichlorophenyl)cyclopropyl-1-carbinol
1-(4-Methylphenyl)cyclopropyl-1-carbinol
1-(4-Ethylphenyl)cyclopropyl-1-carbinol
1-(4-tert-Butylphenyl)cyclopropyl-1-carbinol
1-(4-Methoxyphenyl)cyclopropyl-1-carbinol
1-(4-Ethoxyphenyl)cyclopropyl-1-carbinol
1-(4-n-Propyloxyphenyl)cyclopropyl-1-carbinol
1-(4-iso-Propyloxyphenyl)cyclopropyl-1-carbinol
1-(4-n-Butyloxyphenyl)cyclopropyl-1-carbinol
1-(4-Difluoromethoxyphenyl)cyclopropyl-1-carbinol
1-[4-(2,2,2-Trifluoroethoxy)phenyl]cyclopropyl-1-carbinol
1-(3,4-Methylenedioxyphenyl)cyclopropyl-1-carbinol
1-(3-Chlorophenyl)cyclopropyl-1-carbinol
1-(4-Ethoxyphenyl)-2,2-difluorocyclopropyl-1-carbinol
1-(4-Chlorophenyl)-2,2-difluorocyclopropyl-1-carbinol 1-(4-Difluoromethoxyphenyl)-2,2-difluorocyclopropyl-1-carbinol 1-[4-(2,2,2-Trifluoroethoxy)phenyl]-2,2-difluorocyclopropyl-1-carbinol In the alcohols as above, 1-phenylcyclopropyl-1-carbinols can be obtained by reducing 1-phenylcyclopropanecarboxylic acids or their esters, as obtained by the methods described in J. Amer. Chem. Soc., 93 (17), 4237–4242 (1971), Khim-Farm, Zh., 14 (2), 40–45 (1980) and the like, with a reducing agent such as lithium aluminum hydride, etc.

Also, as a halide represented by the formula (II), the following compounds may be given:
3-Phenoxybenzyl bromide
4-Fluoro-3-phenoxybenzyl chloride
3-(4-Fluorophenoxy)benzyl bromide
3-(4-Chlorophenoxy)benzyl bromide
3-(4-Bromophenoxy)benzyl bromide
3-(4-Methylphenoxy)benzyl chloride
4-Fluoro-3-(4-fluorophenoxy)benzyl chloride
4-Fluoro-3-(4-chlorophenoxy)benzyl chloride
4-Fluoro-3-(4-methylphenoxy)benzyl bromide
4-Fluoro-3-(4-bromophenoxy)benzyl bromide
3-Benzylbenzyl chloride
3-(4-Fluorobenzyl)benzyl bromide
3-(4-Chlorobenzyl)benzyl bromide
3-(4-Bromobenzyl)benzyl bromide
3-(4-Methylbenzyl)benzyl bromide
3-Anilinobenzyl bromide
3-(4-Fluoroanilino)benzyl chloride
3-(4-Chloroanilino)benzyl bromide
3-(4-Bromoanilino)benzyl bromide
3-(4-Methylanilino)benzyl bromide
3-Anilino-4-fluorobenzyl chloride
4-Fluoro-3-(4-fluoroanilino)benzyl chloride
4-Fluoro-3-(4-chloroanilino)benzyl chloride
4-Fluoro-3-(4-bromoanilino)benzyl chloride
4-Fluoro-3-(4-methylanilino)benzyl bromide
3-(3-Fluorophenoxy)benzyl bromide
3-(3-Chlorophenoxy)benzyl bromide
3-(3-Bromophenoxy)benzyl bromide
3-(3-Methylphenoxy)benzyl bromide
4-Fluoro-3-(3-fluorophenoxy)benzyl chloride
4-Fluoro-3-(3-chlorophenoxy)benzyl bromide
4-Fluoro-3-(3-bromophenoxy)benzyl bromide
4-Fluoro-3-(3-methylphenoxy)benzyl chloride
3-(3-Fluorobenzyl)benzyl chloride
3-(3-Chlorobenzyl)benzyl bromide
3-(3-Bromobenzyl)benzyl bromide
3-(3-Methylbenzyl)benzyl bromide
3-(3-Fluoroanilino)benzyl chloride
3-(3-Chloroanilino)benzyl chloride
3-(3-Bromoanilino)benzyl chloride
3-(3-Methylanilino)benzyl bromide
4-Fluoro-3-(3-fluoroanilino)benzyl chloride
4-Fluoro-3-(3-chloroanilino)benzyl chloride
4-Fluoro-3-(3-bromoanilino)benzyl chloride
4-Fluoro-3-(3-methylanilino)benzyl bromide
2-Phenoxy-6-chloromethylpyridine Of the ether compounds represented by the above formula (I), those in which W represents CH group and A represents oxygen atom or imino group, which are represented by the formula,

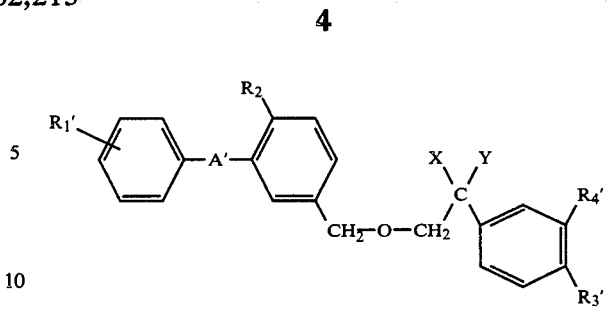

wherein $R_1'$ represents hydrogen atom, fluorine atom, chlorine atom or methyl group, $R_2$ represents hydrogen atom or fluorine atom, $R_3'$ and $R_4'$ are same or different and represent hydrogen atom, fluorine atom, chlorine atom, a $C_{1-4}$ alkyl, a $C_{1-4}$ alkoxy, difluoromethoxy or 2,2,2-trifluoroethoxy group, or represent, taken together, methylenedioxy group, A' represents oxygen atom or imino group, and when the A' represents oxygen atom, X and Y represent, taken together, ethylene group or 1,1-difluoroethylene group, and when the A' represents imino group, both X and Y represent methyl group, or represent, taken together, ethylene group or 1,1-difluoroethylene group, can also be obtained by reacting a benzene derivative represented by the formula (IV),

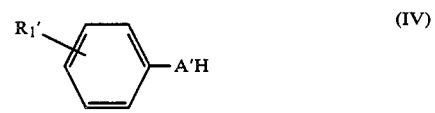

wherein $R_1'$ and A' are as defined above, with a bromobenzene derivative represented by the formula (V),

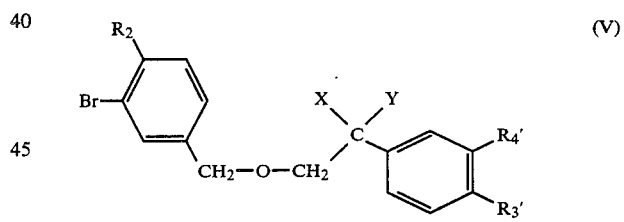

wherein $R_2$, $R_3'$, $R_4'$, X and Y are as defined above, in the presence of a base and copper or a copper compound.

Further, of the ether compounds represented by the formula (I), those in which W represents CH group and A represents imino group, which are represented by the formula,

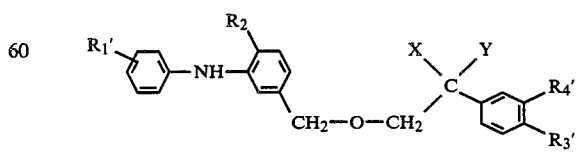

wherein $R_1'$, $R_2$, $R_3'$, $R_4'$, X and Y are as defined above, can be obtained more efficiently by reacting an acetanilide represented by the formula (VI),

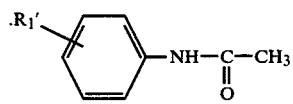

(VI)

wherein R₁' is as defined above, with a bromobenzene derivative represented by the foregoing formula (V) in the presence of a base and copper or a copper compound, followed by deacetylation in the presence of a base.

As the benzene derivative represented by the formula (IV), such compounds as described below are given:
Phenol
2-Fluorophenol
2-Chlorophenol
2-Methylphenol
3-Fluorophenol
3-Chlorophenol
3-Methylphenol
4-Fluorophenol
4-Chlorophenol
4-Methylphenol
Aniline
2-Fluoroaniline
2-Chloroaniline
2-Methylaniline
3-Fluoroaniline
3-Chloroaniline
3-Methylaniline
4-Fluoroaniline
4-Chloroaniline
4-Methylaniline As the bromobenzene derivative represented by the formula (V), such compounds as described below are given:
3-Bromobenzyl 2,2-dimethyl-2-(4-fluorophenyl)ethyl ether
3-Bromobenzyl 2,2-dimethyl-2-(4-chlorophenyl)ethyl ether
3-Bromobenzyl 2,2-dimethyl-2-(4-methylphenyl)ethyl ether
3-Bromobenzyl 2,2-dimethyl-2-(4-ethylphenyl)ethyl ether
3-Bromobenzyl 2,2-dimethyl-2-(4-tert-butylphenyl)ethyl ether
3-Bromobenzyl 2,2-dimethyl-2-(4-methoxyphenyl)ethyl ether
3-Bromobenzyl 2,2-dimethyl-2-(4-ethoxyphenyl)ethyl ether
3-Bromobenzyl 2,2-dimethyl-2-(4-n-propyloxyphenyl)ethyl ether
3-Bromobenzyl 2,2-dimethyl-2-(4-iso-propyloxyphenyl)ethyl ether
3-Bromobenzyl 2,2-dimethyl-2-(4-n-butyloxyphenyl)ethyl ether
3-Bromobenzyl 2,2-dimethyl-2-(4-difluoromethoxyphenyl)ethyl ether
3-Bromobenzyl 2,2-dimethyl-2-[4-(2,2,2-trifluoroethoxy)phenyl]ethyl ether
3-Bromobenzyl 2,2-dimethyl-2-(3,4-methylenedioxyphenyl)ethyl ether
3-Bromobenzyl 2,2-dimethyl-2-(3-chlorophenyl)ethyl ether
3-Bromobenzyl 1-(4-fluorophenyl)cyclopropylmethyl ether
3-Bromobenzyl 1-(4-chlorophenyl)cyclopropylmethyl ether
3-Bromobenzyl 1-(4-methylphenyl)cyclopropylmethyl ether
3-Bromobenzyl 1-(4-ethylphenyl)cyclopropylmethyl ether
3-Bromobenzyl 1-(4-tert-butylphenyl)cyclopropylmethyl ether
3-Bromobenzyl 1-(4-methoxyphenyl)cyclopropylmethyl ether
3-Bromobenzyl 1-(4-ethoxyphenyl)cyclopropylmethyl ether
3-Bromobenzyl 1-(4-n-propyloxyphenyl)cyclopropylmethyl ether
3-Bromobenzyl 1-(4-iso-propyloxyphenyl)cyclopropylmethyl ether
3-Bromobenzyl 1-(4-n-butyloxyphenyl)cyclopropylmethyl ether
3-Bromobenzyl 1-(4-difluoromethoxyphenyl)cyclopropylmethyl ether
3-Bromobenzyl 1-[4-(2,2,2-trifluoroethoxy)phenyl]cyclopropylmethyl ether
3-Bromobenzyl 1-(3,4-methylenedioxyphenyl)cyclopropylmethyl ether
3-Bromobenzyl 1-(3-chlorophenyl)cyclopropylmethyl ether
3-Bromobenzyl 1-(4-ethoxyphenyl)-2,2-difluorocyclopropylmethyl ether
3-Bromobenzyl 1-(4-chlorophenyl)-2,2-difluorocyclopropylmethyl ether
3-Bromobenzyl 1-(4-difluoromethoxyphenyl)-2,2-difluorocyclopropylmethyl ether
3-Bromobenzyl 1-[4-(2,2,2-trifluoroethoxy)phenyl]-2,2-difluorocyclopropylmethyl ether
3-Bromo-4-fluorobenzyl 2,2-dimethyl-2-(4-fluorophenyl)ethyl ether
3-Bromo-4-fluorobenzyl 2,2-dimethyl-2-(4-chlorophenyl)ethyl ether
3-Bromo-4-fluorobenzyl 2,2-dimethyl-2-(4-methylphenyl)ethyl ether
3-Bromo-4-fluorobenzyl 2,2-dimethyl-2-(4-ethylphenyl)ethyl ether
3-Bromo-4-fluorobenzyl 2,2-dimethyl-2-(4-tert-butylphenyl)ethyl ether
3-Bromo-4-fluorobenzyl 2,2-dimethyl-2-(4-methoxyphenyl)ethyl ether
3-Bromo-4-fluorobenzyl 2,2-dimethyl-2-(4-ethoxyphenyl)ethyl ether
3-Bromo-4-fluorobenzyl 2,2-dimethyl-2-(4-n-propyloxyphenyl)ethyl ether
3-Bromo-4-fluorobenzyl 2,2-dimethyl-2-(4-iso-propyloxyphenyl)ethyl ether
3-Bromo-4-fluorobenzyl 2,2-dimethyl-2-(4-n-butyloxyphenyl)ethyl ether
3-Bromo-4-fluorobenzyl 2,2-dimethyl-2-(4-difluoromethoxyphenyl)ethyl ether
3-Bromo-4-fluorobenzyl 2,2-dimethyl-2-[4-(2,2,2-trifluoroethoxy)phenyl]ethyl ether
3-Bromo-4-fluorobenzyl 2,2-dimethyl-2-(3,4-methylenedioxyphenyl)ethyl ether
3-Bromo-4-fluorobenzyl 2,2-dimethyl-2-(3-chlorophenyl)ethyl ether
3-Bromo-4-fluorobenzyl 1-(4-fluorophenyl)cyclopropylmethyl ether
3-Bromo-4-fluorobenzyl 1-(4-chlorophenyl)cyclopropylmethyl ether
3-Bromo-4-fluorobenzyl 1-(4-methylphenyl)cyclopropylmethyl ether 3-Bromo-4-fluorobenzyl 1-(4-ethylphenyl)cyclopropylmethyl ether
3-Bromo-4-fluorobenzyl 1-(4-tert-butylphenyl)cyclopropylmethyl ether
3-Bromo-4-fluorobenzyl 1-(4-methoxyphenyl)cyclopropylmethyl ether
3-Bromo-4-fluorobenzyl 1-(4-ethoxyphenyl)cyclopropylmethyl ether
3-Bromo-4-fluorobenzyl 1-(4-n-propyloxyphenyl)cyclopropylmethyl ether
3-Bromo-4-fluorobenzyl 1-(4-iso-propyloxyphenyl)cyclopropylmethyl ether
3-Bromo-4-fluorobenzyl 1-(4-n-butyloxyphenyl)cyclopropylmethyl ether
3-Bromo-4-fluorobenzyl 1-(4-difluoromethoxyphenyl)cyclopropylmethyl ether
3-Bromo-4-fluorobenzyl 1-[4-(2,2,2-trifluoroethoxy)phenyl]cyclopropylmethyl ether
3-Bromo-4-fluorobenzyl 1-(3,4-methylenedioxyphenyl)cyclopropylmethyl ether
3-Bromo-4-fluorobenzyl 1-(3-chlorophenyl)cyclopropylmethyl ether
3-Bromo-4-fluorobenzyl 1-(4-ethoxyphenyl)-2,2-difluorocyclopropylmethyl ether
3-Bromo-4-fluorobenzyl 1-(4-chlorophenyl)-2,2-difluorocyclopropylmethyl ether
3-Bromo-4-fluorobenzyl 1-(4-difluoromethoxyphenyl)-2,2-difluorocyclopropylmethyl ether
3-Bromo-4-fluorobenzyl 1-[4-(2,2,2-trifluoroethoxy)phenyl]-2,2-difluorocyclopropylmethyl ether The foregoing bromobenzene derivatives are obtained, for example, by reacting the alkali metal salt of an alcohol represented by the formula (VII),

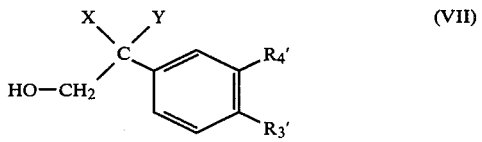

(VII)

wherein $R_3'$, $R_4'$, X and Y are as defined above, with a halide represented by the formula (VIII),

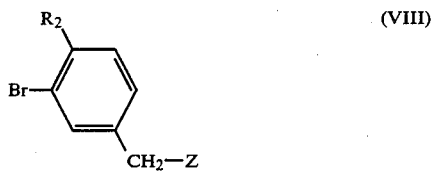

(VIII)

wherein $R_2$ and Z are as defined above.

As the acetanilide represented by the foregoing formula (VI), such compounds as described below are given:
Acetanilide
4'-Fluoroacetanilide
4'-Chloroacetanilide
4'-Methylacetanilide
3'-Fluoroacetanilide
3'-Chloroacetanilide
3'-Methylacetanilide Next, production examples for the compounds of the present invention will be shown.

PRODUCTION EXAMPLE 1

Synthesis of the Compound (2)

264 Milligrams (6.6 mmole) of sodium hydride (as 60% oil suspension) was suspended in 10 ml of dimethylformamide, and a solution of 1.20 g (6.6 mmole) of 1-(4-chlorophenyl)cyclopropyl-1-carbinol in 3 ml of dimethylformamide was added dropwise. The temperature of the mixture was then kept at 50° C. to 100° C. until the evolution of hydrogen came to an end.

Thereafter, the reaction mixture was cooled to room temperature, and a solution of 1.42 g (6.0 mmole) of 3-phenoxy-4-fluorobenzyl chloride in 3 ml of dimethylformamide was added dropwise, followed by stirring overnight at room temperature as it was. The reaction mixture was then poured into 50 ml of water, and extracted with two 20 ml portions of ether. After drying the ether layer over anhydrous magnesium sulfate, ether was removed by evaporation, and the residue was separation-purified by column chromatography on silica gel to obtain 1.97 g of 3-phenoxy-4-fluorobenzyl 1-(4-chlorophenyl)cyclopropylmethyl ether as a colorless liquid.

PRODUCTION EXAMPLE 2

Synthesis of the Compound (22)

2.37 Grams of 3-bromo-4-fluorobenzyl 2,2-dimethyl-2-(4-ethoxyphenyl)ethyl ether, 0.95 g of potassium carbonate, 1.01 g of acetanilide, 10 ml of dimethylformamide and 250 mg of cuprous chloride were mixed and stirred at 140° C. for 40 hours in a nitrogen stream. The reaction mixture was poured into ice water and extracted with ethyl acetate. The ethyl acetate layer was washed with an aqueous sodium chloride liquor, and after removing the solvent by evaporation, the residual oil was dissolved in a 20% ethanol solution of potassium hydroxide (2 times by mole) and refluxed for 30 minutes. The reaction solution was then poured into ice water and extracted with ether. The ether layer was washed with an aqueous sodium chloride liquor and dried over anhydrous magnesium sulfate, and the solvent was removed by evaporation. The residual oil was separation-purified by column chromatography on silica gel to obtain 1.05 g of 3-anilino-4-fluorobenzyl 2,2-dimethyl-2-(4-ethoxyphenyl)ethyl ether.

PRODUCTION EXAMPLE 3

Synthesis of the Compound (25)

132 Milligrams (3.3 mmoles) of sodium hydride (as 60% oil suspension) was suspended in 5 ml of dimethylformamide, and to the resulting suspension was added dropwise a solution of 789 mg (3.0 mmole) of 3-Phenoxybenzyl bromide and 752 mg (3.3 mmole) of 1-(4-ethoxyphenyl)-2,2-difluorocyclopropyl-1-carbinol in 3 ml of dimethylformamide. Stirring was then continued at an inner temperature of 40° C. to 50° C. until the evolution of hydrogen came to an end. Thereafter, the reaction mixture was cooled to room temperature and stirred overnight. The reaction mixture was then poured into 50 ml of water and extracted with two 20-ml portions of ether. The ether layer was dried over anhydrous magnesium sulfate, and after removing ether by evaporation, the residue was separation-purified by column chromatography on silica gel to obtain 1.09 g of 3-phenoxybenzyl 1-(4-ethoxyphenyl)-2,2-difluorocyclopropylmethyl ether as a colorless liquid.

Some of the compounds of the present invention which can be produced according to the foregoing production examples are collectively shown in Table 1.

TABLE 1

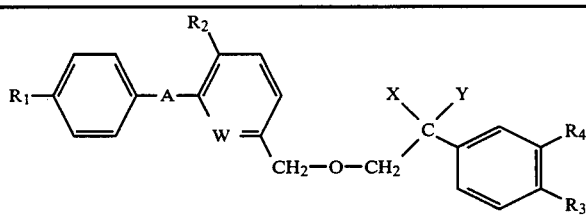

| Compound No. | Structure* | | | | | | | Physical property |
|---|---|---|---|---|---|---|---|---|
| | W | $R_1$ | A | $R_2$ | X | Y | $R_3$ | $R_4$ | |
| 1 | CH | H | O | H | —CH$_2$CH$_2$— | | Cl | H | $n_D^{21.5}$ 1.5899 |
| 2 | ″ | ″ | ″ | F | ″ | | ″ | ″ | $n_D^{21.0}$ 1.5752 |
| 3 | ″ | ″ | ″ | H | ″ | | t-C$_4$H$_9$ | ″ | $n_D^{21.5}$ 1.5685 |
| 4 | ″ | ″ | ″ | F | ″ | | ″ | ″ | $n_D^{23.0}$ 1.5526 |
| 5 | ″ | ″ | ″ | H | ″ | | OC$_2$H$_5$ | ″ | $n_D^{22.0}$ 1.5718 |
| 6 | ″ | ″ | ″ | F | ″ | | ″ | ″ | $n_D^{23.5}$ 1.5569 |
| 7 | ″ | p-Br | ″ | ″ | ″ | | ″ | ″ | $n_D^{23.0}$ 1.5673 |
| 8 | ″ | p-F | ″ | H | ″ | | ″ | ″ | $n_D^{23.5}$ 1.5582 |
| 9 | ″ | H | ″ | F | ″ | | O—n-C$_3$H$_7$ | ″ | $n_D^{21.0}$ 1.5937 |
| 10 | ″ | ″ | ″ | ″ | ″ | | O—iso-C$_3$H$_7$ | ″ | $n_D^{21.5}$ 1.5944 |
| 11 | ″ | ″ | ″ | ″ | ″ | | O—n-C$_4$H$_9$ | ″ | $n_D^{22.5}$ 1.5920 |
| 12 | ″ | ″ | ″ | H | ″ | | OCH$_2$CF$_3$ | ″ | $n_D^{23.0}$ 1.5031 |
| 13 | ″ | ″ | ″ | F | ″ | | ″ | ″ | $n_D^{21.5}$ 1.4852 |
| 14 | ″ | ″ | ″ | ″ | ″ | | —O—CH$_2$— | —O— | $n_D^{21.0}$ 1.5831 |
| 15 | ″ | ″ | CH$_2$ | H | ″ | | OC$_2$H$_5$ | H | $n_D^{20.5}$ 1.5726 |
| 16 | ″ | ″ | ″ | ″ | ″ | | t-C$_4$H$_9$ | ″ | $n_D^{21.0}$ 1.5692 |
| 17 | ″ | ″ | ″ | ″ | ″ | | OCH$_2$CF$_3$ | ″ | $n_D^{19.0}$ 1.5045 |
| 18 | ″ | ″ | NH | F | ″ | | OC$_2$H$_5$ | ″ | $n_D^{22.0}$ 1.5781 |
| 19 | ″ | ″ | ″ | H | CH$_3$ | CH$_3$ | t-C$_4$H$_9$ | ″ | $n_D^{21.0}$ 1.5751 |
| 20 | ″ | ″ | ″ | F | ″ | ″ | Cl | ″ | $n_D^{22.0}$ 1.5861 |
| 21 | ″ | ″ | ″ | ″ | ″ | ″ | ″ | Cl | $n_D^{20.0}$ 1.5936 |
| 22 | ″ | ″ | ″ | ″ | ″ | ″ | OC$_2$H$_5$ | H | $n_D^{22.0}$ 1.5682 |
| 23 | ″ | Cl | ″ | H | ″ | ″ | ″ | ″ | $n_D^{21.5}$ 1.5731 |
| 24 | N | H | O | ″ | ″ | ″ | ″ | ″ | $n_D^{24.0}$ 1.5640 |
| 25 | CH | ″ | ″ | ″ | —CH$_2$—CF$_2$— | | ″ | ″ | $n_D^{23.0}$ 1.5581 |

*Examples of the substituents $R_1$, $R_2$, A, X, Y, $R_3$ and $R_4$, of the foregoing formula.

REFERENCE EXAMPLE 1

Synthesis of 1-(4-ethoxyphenyl)cyclopropyl-1-carbinol

445 Milligrams (11.7 mmole) of lithium aluminum hydride was suspended in 40 ml of tetrahydrofuran in a nitrogen stream, and to the resulting suspension was added dropwise a solution of 2.41 g (11.7 mmole) of 1-(4-ethoxyphenyl)cyclopropanecarboxylic acid in 20 ml of tetrahydrofuran with stirring and with ice-cooling. After completion of the dropwise addition, the reaction mixture was stirred at room temperature for 2 hours.

Thereafter, the reaction solution was carefully poured into a large quantity of ice/conc. hydrochloric acid mixture with stirring, and extracted with diethyl ether several times. The ether layer was dried over anhydrous magnesium sulfate, and the solvent was removed by evaporation to obtain 2.13 g of 1-(4-ethoxyphenyl)cyclopropyl-1-carbinol as a pale yellow liquid. $n_D^{21.0}$ 1.5382

REFERENCE EXAMPLE 2

Synthesis of 1-(4-chlorophenyl)cyclopropyl-1-carbinol

668 Milligrams (17.6 mmole) of lithium aluminum hydride was suspended in 60 ml of tetrahydrofuran in a nitrogen stream, and to the resulting suspension was added dropwise a solution of 3.46 g (17.6 mmole) of 1-(4-chlorophenyl)cyclopropanecarboxylic acid in 30 ml of tetrahydrofuran with stirring and with ice-cooling. After completion of the dropwise addition, the reaction mixture was stirred at room temperature for 2 hours.

Thereafter, the reaction solution was carefully poured into a large quantity of ice/conc. hydrochloric acid mixture with stirring, and extracted with diethyl ether several times. The ether layer was dried over anhydrous magnesium sulfate, and the solvent was removed by evaporation to obtain 2.98 g of 1-(4-chlorophenyl)cyclopropyl-1-carbinol as a pale yellow liquid.

$^1$H-NMR spectrum (CDCl$_3$, TMS). δ 7.28 (4H, s), δ 3.63 (2H, s), δ 1.50 (1H, broad s), δ 0.83 (4H, s).

REFERENCE EXAMPLE 3

Synthesis of 1-(4-ethoxyphenyl)-2,2-difluorocyclopropyl-1-carbinol 3.5 Grams of ethyl α-(4-ethoxyphenyl)acrylate was dissolved in 50 ml of dry dimethoxyethane and heated to 150° C. to 160° C. To this solution was added dropwise a solution of 17.0 g of sodium difluorochloroacetate in 250 ml of dry dimethoxyethane over about 1 hour. After completion of the dropwise addition, heating and stirring were continued at 150° C. to 160° C. for about 10 minutes. Thereafter, the reaction solution was cooled to room temperature, poured into ice water and extracted with ether two times. The ether layer was dried over anhydrous magnesium sulfate, and after removing the solvent under reduced pressure, the residue was purified by column chromatography on a column packed with 100 g of silica gel using a n-hexane/ethyl acetate (20:1) mixture as a eluting solvent, to obtain 3.50 g of ethyl 1-(4-ethoxyphenyl)-2,2-difluorocyclopropanecarboxylate $^1$N-NMR spectrum (CDCl$_3$, TMS). δ 1.18 (3H, t), δ 1.39 (3H, t), δ 1.81 (1H, ddd), δ 2.51 (1H, ddd).

Thereafter, 1.0 g of this ethyl 1-(4-ethoxyphenyl)-2,2-difluorocyclopropanecarboxylate was dissolved in 10 ml of dry ether and added dropwise over 5 minutes to a suspension of 141 mg of lithium aluminum hydride in 50 ml of dry ether previously cooled to 0° C. to 5° C. After stirring was continued at the same temperature for 30 minutes, the reaction solution was poured into a cooled aqueous dilute hydrochloric acid. The ether layer was separated, washed twice with a saturated aqueous sodium chloride solution and dried over anhydrous magnesium sulfate. The solvent was then removed under reduced pressure to obtain 0.82 g of 1-(4-ethoxyphenyl)-2,2-difluorocyclopropyl-1-carbinol.

$^1$H-NMR spectrum (CDCl$_3$, TMS). δ 1.36 (3H, t), δ 3.23 (2H, s), δ 3.94 (2H, g), m.p. 89.8° C.

REFERENCE EXAMPLE 4

Synthesis of 3-bromo-4-fluorobenzyl 2,2-dimethyl-2-(4-ethoxyphenyl)ethyl ether

657 Milligrams of sodium hydride (as 60% oil suspension) was added to 10 ml of dimethylformamide, and 3.19 g of 2,2-dimethyl-2-(4-ethoxyphenyl)ethanol was added dropwise. Thereafter, the reaction solution was warmed to 50° C. and stirred for 10 minutes, and 4.0 g of 3-bromo-4-fluorobenzyl bromide was added dropwise thereto at 20° C. After completion of the dropwise addition, stirring was continued at 50° C. for further 5 hours, and the reaction solution was then poured into a 5% hydrochloric acid/ice water mixture and extracted with ethyl acetate. The ethyl acetate layer was washed with an aqueous sodium chloride liquor and dried over anhydrous magnesium sulfate. After removing the solvent by evaporation, the residual oil was purified by column chromatography on a column packed with 60 g of silica gel to obtain 2.37 g of 3-bromo-4-fluorobenzyl 2,2-dimethyl-2-(4-ethoxyphenyl)ethyl ether. $^1$H-NMR spectrum (CDCl$_3$, TMS). δ 7.4–6.5 (7H, m), δ 4.30 (2H, s), δ 3.99 (2H, q), δ 3.34 (2H, s), δ 1.36 (3H, t), δ 1.30 (6H, s).

REFERENCE EXAMPLE 5

Synthesis of 3-anilino-4-fluorobenzyl chloride

Two grams of phosphorus oxychloride was added to 470 mg of 3-anilino-4-fluorobenzyl alcohol with ice-cooling, and the mixture was stirred for 1 hour and then for further 12 hours at 15° C. Thereafter, the reaction solution was poured into a 10% aqueous potassium carbonate solution and extracted with ethyl acetate. The ethyl acetate layer was washed with an aqueous sodium chloride liquor and dried over anhydrous magnesium sulfate. The solvent was then removed by evaporation to obtain 450 mg of 3-anilino-4-fluorobenzyl chloride.

$n_D^{22}$ 1.6275.

$^1$H-NMR spectrum (CDCl$_3$, TMS). δ 4.38 (2H, s).

When the compounds of the present invention are used as an active ingredient for an insecticidal and/or acaricidal composition, they are generally mixed with solid, liquid or gaseous carriers or other assistants for preparation (e.g. surfactants, dispersing agents, wetting agents, stabilizers) to make them various kinds of preparation such as emulsifiable concentrates, wettable powders, dusts, granules, oil sprays, aerosols, heating-fumigants (e.g. mosquito coils, electric mosquito fumigators), foggings, non-heating fumigants, poisonous baits and the like.

The content of active ingredient of these preparations is 0.1 to 95% by weight.

As the solid carrier, there may be given for example fine powders to powdery products of clays (e.g. kaolin, bentonite, terra abla, pyrophyllite, sericite), talcs, other inorganic minerals (e.g. hydrated silicon dioxide, pumice, diatomaceous earth, sulfur powder, activated carbon) and the like.

As the liquid carrier, there may be given for example alcohols (e.g. methyl alcohol), ketones (e.g. acetone, methyl ethyl ketone), ethers (e.g. ethyl ether, dioxane, cellosolve, tetrahydrofuran), aromatic hydrocarbons (e.g. benzene, toluene, xylene, methylnapthalene), aliphatic hydrocarbons (e.g. kerosene), esters, nitriles, acid amides (e.g. dimethylformamide, dimethylacetamide), halogenated hydrocarbons (e.g. dichloroethane, trichloroethane, carbon tetrachloride) and the like.

As the surfactant, there may be given for example alkyl sulfuric acid esters, alkylsulfonates, alkylarylsulfonates, polyethylene glycol ethers, polyhydric alcohol esters and the like.

Further, the usable fixing agents and dispersing agents include for example casein, gelatin, starch powder, CMC, gum arabic, alginic acid, ligninsulfonate, bentonite, molasses, polyvinyl alcohol, pine oil, agar and the like. As the stabilizer, there may be given for example PAP (isopropyl phosphate), TCP (tricresyl phosphate), tall oil, epoxidized oil, various surfactants, various fatty acids and their esters.

Next, preparation examples will be shown.

PREPARATION EXAMPLE 1

0.5 Part of each of the compounds (1) to (25) of the present invention is dissolved in deodorized kerosene and made up to 100 parts with kerosene to obtain the oil spray of each compound.

PREPARATION EXAMPLE 2

To 10 parts of each of the compounds (1) to (25) of the present invention are added 10 parts of an emulsifier (Sorpol 3005X, a mixture of a nonionic surfactant and an anionic surfactant) and 80 parts of xylene. The mixture is well mixed with stirring to obtain the emulsifiable concentrate of each compound.

PREPARATION EXAMPLE 3

0.2 Part of the compound (1) of the present invention, 0.3 part of tetramethrin, 5 parts of xylene and 44.5 parts of deodorized kerosene are well mixed to make a solution. The solution is filled in an aerosol container, and after attaching a valve portion to the container, 50 parts of a propellant (liquefied petroleum gas) is charged therein through the valve under pressure to obtain an aerosol.

PREPARATION EXAMPLE 4

0.2 Part of each of the compounds (2) and (6) of the present invention, 0.3 part of the d-trans allethrin, 8.5 parts of deodorized kerosene and 1 part of an emulsifier (Atmos 300, a registered trade mark of Atlas Chemical Co.) are mixed and emulsified with addition of 60 parts of pure water. The emulsion is then filled in an aerosol container together with 30 parts of a 3:1 mixture of deodorized butane and deodorized propane to obtain a water-base aerosol.

PREPARATION EXAMPLE 5

0.6 Gram of the compound (5) of the present invention is dissolved in 20 ml of methanol, and this solution and 99.4 g of a mosquito coil carrier, a 3:5:1 mixture of Tabu powder, Pyrethrum marc and wood powder, are uniformly mixed with stirring after which methanol is evaporated. To the residue is added 150 ml of water, and the mixture is well kneaded, shaped and dried to obtain a mosquito coil.

PREPARATION EXAMPLE 6

To 0.08 g of the compound (5) of the present invention is added 0.08 g of BHT, and the mixture is dissolved in a suitable amount of chloroform. Thereafter, filter paper of 3.5 cm×1.5 cm×0.3 cm (thick) is made to uniformly adsorb the solution.

Thus, a fibrous fumigant composition for heating on hot plate is obtained.

PREPARATION EXAMPLE 7

Ten parts of each of the present compounds (1) and (18) of the present invention is well mixed with 5 parts of an emulsifier (Sorpol 5029-0, a dispersing agent consisting of sodium lauryl sulfate), and 85 parts of 300-mesh diatomaceous earth is added thereto. The mixture is well mixed with stirring in a mortar to obtain the wettable powder of each compound.

PREPARATION EXAMPLE 8

0.5 Part of each of the compounds (1) to (25) of the present invention is dissolved in a suitable amount of acetone, and 99.5 parts of 300-mesh talc is added thereto. The mixture is well mixed with stirring, and acetone is removed by evaporation to obtain the dust of each compound.

The compounds of the present invention are widely used as an insecticidal and/or acaricidal composition for agriculture and horticulture in paddy field, plowland, orchard, tea garden, mulberry field, turf, pasture, forest and the like as well as an insecticidal and/or acaricidal composition for household.

Next, the usefulness of the compounds of the present invention as an active ingredient for an insecticidal and/or acaricidal composition will be illustrated with reference to the following test examples.

The compounds of the present invention are shown by serial numbers in Table 1, and compounds used as a control are shown by the following symbols.

| Control | Structural formula | Remarks |
|---|---|---|
| A | 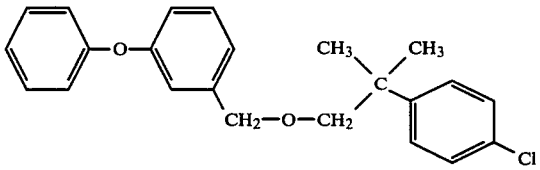 | Compound described in Japanese Patent Application Kokai (Laid-open) No. 56438/1982 and French Patent No. 8108642. |
| B | 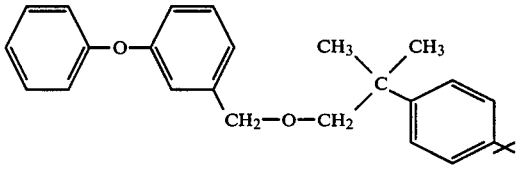 | Compound described in Japanese Patent Application Kokai (Laid-open) No. 154427/1981. |
| C | 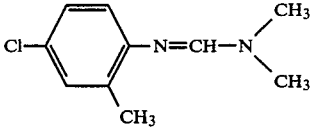 | 1000-Fold dilute liquor of 50% emulsifiable concentrate of chlorodimeform |
| D | 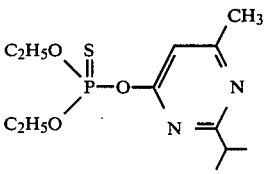 | Diazinon |

TEST EXAMPLE 1

On the bottom of a polyethylene cup of 5.5 cm in diameter was placed a piece of filter paper of the same size as the bottom, and 0.7 ml of a 200-field aqueous dilute liquor (corresponding to 500 ppm) of the emulsifiable concentrate obtained in Preparation Example 2 was dropped down to the filter paper. Thirty milligrams of sucrose was placed on the filter paper as bait. Thereafter, 10 adult female houseflies (*Musca domestica*) were liberated in the cup which was then covered with a lid. After 48 hours, the dead and alive were examined to obtain mortality (2 replications).

| Test compound | Mortality (%) |
|---|---|
| Compound (1) | 100 |
| Compound (2) | 100 |
| Compound (5) | 100 |
| Compound (6) | 100 |
| Compound (7) | 100 |

| Test compound | Mortality (%) |
| --- | --- |
| Compound (8) | 100 |
| Compound (9) | 100 |
| Compound (10) | 100 |
| Compound (11) | 100 |
| Compound (12) | 100 |
| Compound (13) | 100 |
| Compound (14) | 100 |
| Compound (15) | 100 |
| Compound (17) | 100 |
| Compound (18) | 100 |
| Compound (20) | 100 |
| Compound (21) | 100 |
| Compound (22) | 100 |
| Compound (23) | 100 |
| Compound (24) | 100 |
| Compound (25) | 100 |
| No treatment | 0 |

TEST EXAMPLE 2

Aqueous dilute liquors of a pre-determined concentration, as prepared from the emulsifiable concentrates of the compounds (2), (5), (6), (14), (24) and (25) of the present invention obtained in Preparation Example 2 as well as those of the control compounds (A) and (B) similarly obtained, were each treated in the same manner as in Test Example 1 to obtain a $LC_{50}$ value (median lethal concentration) on adult female housefly (2 replications).

| Test compound | $LC_{50}$ (ppm) |
| --- | --- |
| Compound (2) | 24 |
| Compound (5) | 34 |
| Compound (6) | 19 |
| Compound (14) | 14 |
| Compound (24) | 14 |
| Compound (25) | 21 |
| Control A | 58 |
| Control B | >100 |

TEST EXAMPLE 3

Two milliliters of a 200-fold aqueous dilute liquor (corresponding to 500 ppm), as prepared from the emulsifiable concentrate of the compound of the present invention obtained in Preparation Example 2, was infiltrated into artificial feeds for tobacco cutworm (*Spodoptera litura*) which were then placed in a polyethylene cup of 11 cm in diameter. Thereafter, 10 third instar larvae of tobacco cutworm were liberated in the cup, and after 24 hours, the dead and alive of the larvae were examined to obtain mortality (2 replications).

| Test compound | Mortality (%) |
| --- | --- |
| Compound (1) | 100 |
| Compound (2) | 100 |
| Compound (3) | 100 |
| Compound (4) | 100 |
| Compound (5) | 100 |
| Compound (6) | 100 |
| Compound (7) | 100 |
| Compound (8) | 100 |
| Comopund (9) | 100 |
| Compound (10) | 100 |
| Compound (11) | 100 |
| Compound (12) | 100 |
| Compound (13) | 100 |
| Compound (14) | 100 |
| Compound (15) | 100 |
| Compound (16) | 100 |
| Compound (17) | 100 |
| Compound (18) | 100 |
| Compound (19) | 100 |
| Compound (20) | 100 |
| Compound (21) | 100 |
| Compound (22) | 100 |
| Compound (23) | 100 |
| Compound (24) | 100 |
| Compound (25) | 100 |
| No treatment | 0 |

TEST EXAMPLE 4

Aqueous dilute liquors of a pre-determined concentration, as prepared from the emulsifiable concentrates of the compounds (2), (6), (20) and (25) of the present invention obtained in Preparation Example 2 as well as that of the control compound (A) similarly obtained, were each treated in the same manner as in Test Example 3 to obtain a $LC_{50}$ value (median lethal concentration) on the third instar larvae of tobacco cutworm (2 replications).

| Test compound | $LC_{50}$ (ppm) |
| --- | --- |
| Compound (2) | 8.3 |
| Compound (6) | 4.4 |
| Compound (20) | 7.8 |
| Compound (25) | 7.0 |
| Control A | 12.5 |

TEST EXAMPLE 5

Ten adult female carmine mites (*Tetranychus cinnabarinus*) were made parasitic on the one leaf/four leaves of potted kidney bean which had elapsed 5 days after sowing. The plant was then stored in a constant temperature room kept at 27° C. After six days, 200-fold aqueous dilute liquors (corresponding to 500 ppm), as prepared from the emulsifiable concentrates of the compounds (4), (5), (6), (13), (18), (20), (24) and (25) of the present invention obtained in Preparation Example 2 as well as that of the control compound (C) similarly obtained, were each sprayed on the kidney bean at a rate of 10 ml/pot by means of a turn table. After six days, the number of the female adults on the plant was counted. Standard for the judgement of the effect:

++: 0 to 9 parasitic adult females on one leaf.
+: 10 to 30 parasitic adult females on one leaf.
−: 31 or more parasitic adult females on one leaf.

The result is shown below:

| Test compound | Judgement |
| --- | --- |
| Compound (4) | ++ |
| Compound (5) | ++ |
| Compound (6) | ++ |
| Compound (13) | ++ |
| Compound (18) | ++ |
| Compound (20) | ++ |
| Compound (24) | ++ |
| Compound (25) | ++ |
| Control C | ++ |
| No treatment | − |

TEST EXAMPLE 6

Rice plants were grown in a 1/10,000 Wagner's pot for 45 days after sowing, and aqueous dilute liquors of a pre-determined concentration, as prepared from the emulsifiable concentrate of the compound (1) of the present invention obtained in Preparation Example 2 as well as those of the control compounds (A) and (D) similarly obtained, were each sprayed on the plants at a rate of 10 ml/pot. After covering the pot with a wire net, about 15 adult green rice leaf hoppers (*Nephotettix cincticeps*) having a resistance to organophosphate and carbamate insecticides were liberated therein at the day of spraying, two days and seven days after spraying. At the day of spraying, the number of knocked down insects was counted for 180 minutes after liberation of the insects to obtain a $KT_{50}$ value (a period of time required for 50% of the insects to be knocked down). The dead and alive were examined after 24 hours (2 replications).

| Test compound | Spray concentration (ppm) | $KT_{50}$ (min) | Number of days elapsed after spraying and mortality (%) | | |
|---|---|---|---|---|---|
| | | | 0 (day) | 2 (day) | 7 (day) |
| Compound (1) | 10 | >180 | 97 | 3 | — |
| | 50 | 58 | 100 | 84 | 27 |
| Control A | 10 | >180 | 63 | 3 | — |
| | 50 | ≈180 | 100 | 88 | 3 |
| Control D | 500 | >180 | 41 | 0 | — |
| No treatment | — | >180 | 0 | 0 | 3 |

What is claimed is:

1. A compound of the formula,

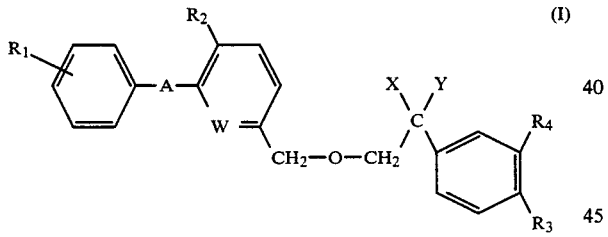

wherein W represents CH or nitrogen, and
   (1) when W is CH, $R_1$ represents hydrogen, fluorine, chlorine, bromine or methyl, $R_2$ represents hydrogen or fluorine, $R_3$ and $R_4$ are same or different and represent hydrogen, halogen, $C_{1-4}$ alkyl, a $C_{1-4}$ alkoxy, difluoromethoxy or 2,2,2-trifluoroethoxy, or represent, taken together, methylenedioxy, A represents oxygen, and X and Y represent, taken together, ethylene or 1,1-difluoroethylene which form a cyclopropyl ring or a 1,1-difluorocyclopropyl ring with a carbon to which they are attached, and
   (2) when W is nitrogen, both $R_1$ and $R_2$ represent hydrogen, and $R_3$, $R_4$, A, X and Y are as defined above.

2. The compound according to claim 1, wherein X and Y represent, taken together, ethylene.

3. The compound according to claim 1, wherein X and Y represent, taken together, 1,1-difluoroethylene.

4. The compound according to claim 1, wherein $R_3$ is a $C_{1-4}$ alkoxy and $R_4$ is hydrogen.

5. The compound according to claim 1, wherein $R_3$ is ethoxy and $R_4$ is hydrogen.

6. A compound of the formula,

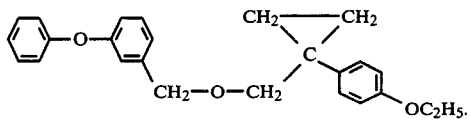

7. A compound of the formula,

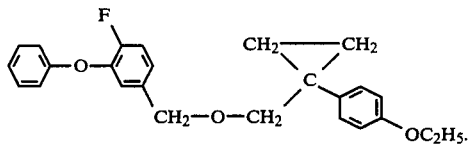

8. A compound of the formula,

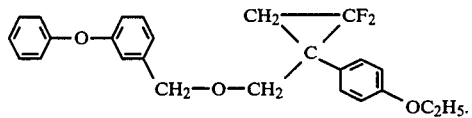

9. A compound of the formula

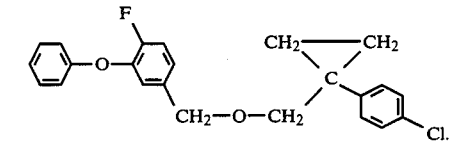

10. A compound of the formula,

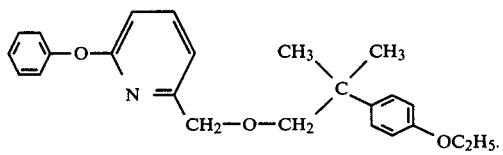

11. An insecticidal and/or acaricidal composition which comprises as an active ingredient an insecticidally and/or acaricidally effective amount of the compound according to claim 1 and an inert carrier.

12. A method for controlling an insect and/or acarid which comprises applying an insecticidally and/or acaricidally effective amount of the compound according to claim 1 to the insect and/or acarid.

13. The compound according to claim 1 wherein W represents CH.

14. An insecticidal and/or acaricidal composition which comprises as an active ingredient an insecticidally and/or acaricidally effective amount of the compound according to claim 13 and an inert carrier.

15. An insecticidal and/or acaricidal composition which comprises as an active ingredient an insecticidally and/or acaricidally effective amount of the compound according to claim 2 and an inert carrier.

16. An insecticidal and/or acaricidal composition which comprises as an active ingredient an insecticidally and/or acaricidally effective amount of the compound according to claim 6 and an inert carrier.

17. A method for controlling an insect and/or acarid which comprises applying an insecticidally and/or acaricidally effective amount of the compound according to claim 13 to the insect and/or acarid.

18. A method for controlling an insect and/or acarid which comprises applying an insecticidally and/or acaricidally effective amount of the compound according to claim 2 to the insect and/or acarid.

19. A method for controlling an insect and/or acarid which comprises applying an insecticidally and/or acaricidally effective amount of the compound according to claim 6 to the insect and/or acarid.

* * * * *